United States Patent [19]

Hozumi et al.

[11] Patent Number: 4,542,219
[45] Date of Patent: Sep. 17, 1985

[54] CERTAIN HETEROCYCLIC AMMONIO PHOSPHATE DERIVATIVES

[75] Inventors: Motoo Hozumi, Omiya; Hiroaki Nomura, Takatsuki; Yoshio Yoshioka, Nara, all of Japan

[73] Assignee: Takeda Chemical Industries, Ltd., Osaka, Japan

[21] Appl. No.: 361,409

[22] Filed: Mar. 24, 1982

[30] Foreign Application Priority Data

Mar. 30, 1981 [JP] Japan ................... 56-48287
Feb. 19, 1982 [JP] Japan ................... 57-26692

[51] Int. Cl.⁴ .......................... C07F 9/58; C07F 9/60; C07F 9/62; C07F 9/65
[52] U.S. Cl. ........................ 546/22; 546/23; 544/157; 544/232; 544/337; 548/112; 260/925; 260/944; 260/945; 514/908
[58] Field of Search ............ 546/22, 23; 548/112; 544/232, 157, 337

[56] References Cited

FOREIGN PATENT DOCUMENTS 772649  2/1978  South Africa ................ 260/945
1280788 7/1972  United Kingdom ......... 260/944

OTHER PUBLICATIONS

Derwent Basic No. 23537A/13, the Abstract of OLS No. 26 42 661.

Primary Examiner—Alan L. Rotman
Attorney, Agent, or Firm—Wegner & Bretschneider

[57] ABSTRACT

Ethylene glycol derivatives, inclusive of salts thereof, which have the formula:

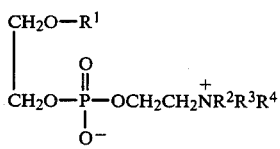

wherein $R^1$ is $C_{8-26}$ aliphatic hydrocarbon residue; $R^2$, $R^3$ and $R^4$ are each hydrogen or lower alkyl which may be substituted, or $-N^+R^2R^3R^4$ represents cyclic ammonio, exhibit inhibitory activity to multiplication of tumor cells and antimicrobial activity.

6 Claims, No Drawings

CERTAIN HETEROCYCLIC AMMONIO PHOSPHATE DERIVATIVES

This invention relates to a novel antitumor agent.

More particularly, this invention relates to an antitumor agent containing ethyleneglycol derivative, inclusive of salts thereof, which has the formula:

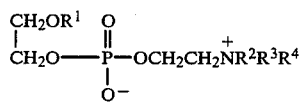
(I)

wherein $R^1$ is $C_{8-26}$ aliphatic hydrocarbon residue; $R^2$, $R^3$ and $R^4$ are each hydrogen or lower alkyl which may be substituted, or $-N^+R^2R^3R^4$ represents cyclic ammonio.

Referring to the above formula (I), $C_{8-26}$ aliphatic hydrocarbon residue is straight-chain or branched, saturated or unsaturated, such as alkyl or alkenyl, and the alkenyl may be Z- or E-configured. These groups may have substituents such as hydroxyl, mercapto, amino, oxo, carbamoyl, carboxyl, halogen, $C_{3-7}$ cycloalkyl, phenyl, etc. $R^1$ includes, for example, $C_{10-20}$ alkyl, e.g. n-dodecyl, n-tridecyl, n-tetradecyl, 3,7,11-trimethyltetradecyl, n-pentadecyl, n-heptadecyl, n-octadecyl, n-eicosanyl, n-docosanyl, dihydrophytyl; $C_{10-20}$ alkenyl, e.g. 8-tridecenyl ($\Delta^8$), 3,7,11-trimethyl-2,6,10-dodecatrienyl, 8-tetradecenyl ($\Delta^8$), 8,11-tetradecadienyl ($\Delta^{8,11}$), 8-heptadecenyl ($\Delta^8$), 1-heptadecenyl ($\Delta^1$), 8,11,14-heptadecatrienyl ($\Delta^{8,11,14}$), 8,11-octadecadienyl ($\Delta^{8,11}$), 4,7,10,13-nonadecatetraenyl ($\Delta^{4,7,10,13}$), phytyl, 12-(2,3-cyclopentenyl)dodecyl, 12-(2,3-cyclopentenyl)-5-dodecenyl, 11-hydroxy-8-heptadecenyl, 3,7-dimethyl-9-(2,6,6-trimethyl-1-cyclohexen-1-yl)-2,4,6,3-nonatetraenyl; $C_{14-24}$ aralkyl, e.g. 15-(4-n-butylphenoxy)pentadecyl, ω-(p-tolyl)heptadecyl, 6-(4-n-pentylphenoxy)-hexadecyl; 4,7,10,13-nonadecatetraenyl, 8-heptadecenyl, etc.

$R^2$, $R^3$ and $R^4$ are each hydrogen or lower alkyl. The lower alkyl includes, for example, $C_{1-5}$ alkyl (e.g. methyl, ethyl, propyl, i-propyl). These groups may have substituent such as hydroxycarbonyl, lower($C_{1-3}$)alkoxycarbonyl, hydroxyl, cyano or lower($C_{1-3}$)alkoxyl. The cyclic ammonio group of $-N^+R^2R^3R^4$ includes for example, pyridinio, oxazolio, thiazolio, pyridazinio, quinolinio, isoquinolinio, etc., each of which may have substituents such as $C_{1-4}$ alkyl (e.g. methyl, ethyl), hydroxyl hydroxyethyl, aminoethyl, amino(imino), carbamoyl, ureido, etc. The cyclic ammonio group may include the case in which two of $R^2$, $R^3$ and $R^4$ form a ring with the quaternary nitrogen atom with the remaining member being, for example, an $C_{1-4}$ alkyl (e.g. methyl, ethyl), such as N-methylmorpholinio, N-methylpiperazinio, etc.

The compound (I) may exist in the form of:

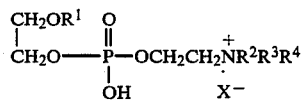
(Ia)

wherein $X^-$ is an anion of Cl, Br or I, or in the form of:

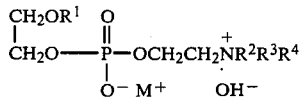
(Ib)

wherein $M^+$ is an alkali metal (e.g. Na, K) ion. The compound (I) can also form a salt with an alkaline earth metal (e.g. Ca, Mg).

Among compounds (I), the compounds represented by formula (I'):

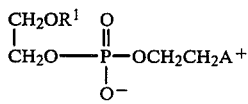
(I')

wherein $R^1$ is as defined above; $A^+$ is cyclic ammonio, and the compounds represented by formula (I''):

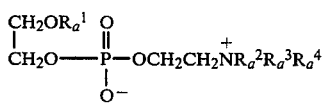
(I'')

wherein $R_a^1$ is $C_{10-15}$ aliphatic hydrocarbon residue; $R_a^2$, $R_a^3$ and $R_a^4$ are each hydrogen or lower alkyl which may be substituted are novel compounds which are especially suited for the purposes of this invention.

Referring to formulas (I') and (I''), the cyclic ammonio group $A^+$ may be the aforementioned cyclic ammonio group represented by $-N^+R^2R^3R^4$. The $C_{10-15}$ aliphatic hydrocarbon residue $R_a^1$ may be one of those aliphatic hydrocarbon residues $R^1$ containing 10 to 15 carbon atoms, and $R_a^2$, $R_a^3$ and $R_a^4$ may be hydrogen or lower alkyl which may be substituted as mentioned for $R^2$, $R^3$ and $R^4$. Salts of (I') and (I'') may be similar to those mentioned for salts.

The compound (I) can be produced for example by the following processes.

Process A

A compound of formula:

(II)

wherein $R^1$ is as defined above, is reacted with a compound of formula:

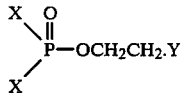
(III)

wherein X and Y are each halogen (e.g. Cl, Br or I), to give a compound of formula:

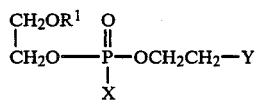
(IV)

wherein $R^1$, X and Y are as defined above, which is then reacted with water to give a compound of formula:

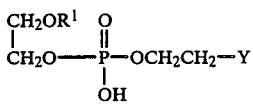

(V)

wherein $R^1$ and Y are as defined above. This compound (V) is reacted with a compound of formula:

$$NR^2R^3R^4 \qquad (VI)$$

wherein all symbols are as defined above, to give the desired compound (I).

In the above process, the compound (II) can be prepared by the known methods, e.g. the method described by Abe Y. and Watanabe S. in Kogyo Kagaku Zasshi (J. Industrial Chemistry of Japan), 66, 1842–1844 (1963) or by A. N. Wrigley et al in J. Org. Chem., 25, 439 (1960).

Where any two or all of $R^2$, $R^3$ are hydrogen, the following process B can also be employed.

Process B

A compound (II) is reacted with a compound of formula:

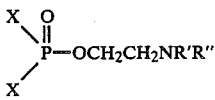

(III')

wherein X is as defined above; either R' or R" is —COOCH$_2$C$_6$H$_5$, —COOC$_6$H$_5$, —CHO, —COCF$_3$, —COCH$_2$C$_6$H$_5$, —SiMe$_3$ or —C(C$_6$H$_5$)$_3$ and the other is hydrogen, or R' and R" are cyclized to form succinimido or phthalimido and the reaction product is further treated with water and, then, deprotected in the per se conventional manner to yield of compound (I) which may be represented by formula:

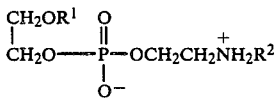

(I''')

wherein $R^1$ and $R^2$ are as defined above.

Process C

A compound of formula (II) is reacted with a phosphorylating agent to give a compound of formula:

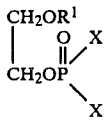

(VII)

wherein $R^1$ and X are as defined above, which is then reacted with a compound of formula:

$$HOCH_2CH_2NR'R'' \qquad (VIII)$$

wherein R' and R" are as defined above, or a compound of formula:

$$HOCH_2CH_2Z \qquad (IX)$$

wherein Z is Y or —N$^+$R$^2$R$^3$R$^4$, to give a compound of formula (V) or (I). The compound (V) can be converted to a compound (I) by the process described hereinbefore. Further, when $R^2$, $R^3$ or/and $R^4$ in formula (I) have ester or cyano as substituent, it can be derived to corresponding carboxylic acid of (I) by hydrolysis, upon necessity.

The compound (I), inclusive of salts thereof, which is active component of the antitumor agent according to this invention have growth inhibiting and cell differentiation (decarcinogenesis) inducing activities against tumor cells (e.g. mouse spontaneous leukemia cells MI, Rauscher virus-induced mouse leukemia cells, human myelogenous leukemia cells HL-60). It also shows antitumor activity in in vivo tumor systems where the rate of tumor growth is relatively low.

In addition to the cytocidal and cell differentiation inducing actions, the compound has host-mediated antitumor activity such as macrophage activation. Specifically, when administered to animals bearing spontaneous carcinomas, carcinogen-induced solid tumors, MM46 derived from carcinoma, Ehrlich carcinoma or sacroma 180, or to nude mice implanted with human cancer cells, the compound displays life-span prolonging effects.

The compound (I) is of relatively low toxicity and has generally low hemolytic activity. Thus, in a hemolysis test (human erythrocytes) by the method of Gottfried et al [J. Lipid Research, 4, 57 (1963)], the 50% hemolytic concentration of the compound according to Production Example 2, for instance, was found to be about 80 µg/ml (in the presence of 5% human albumin). In these compounds (I), the influence of the length of chain $R^1$ varies with the other moiety of the molecule. Generally, Compound (I) having C$_{16-19}$ as R' exhibits the strong cytocidal activity, while one having C$_{12-15}$ exhibits strong activity in cell differentiation and the strong host-mediated antitumor activity such as immunoenhancement is achieved by C$_{19-26}$ compound, and a still greater decrease of hemolysis is obtained when $R^1$ contains a double bond or —N$^+$R$^2$R$^3$R$^4$ is cyclic ammonio such as pyridinio.

The compound (I) is generally available as a crystalline powder or powder and since it is sufficiently hydrophilic and lipophilic, the antitumor compound can be formulated into variety of pharmaceutical compositions such as injections, tablets, capsules, solutions, ointments, etc. for oral or parenteral administration.

Injectable solutions and solutions for drip infusion, for instance, can be prepared in the conventional manner using physiological saline or an aqueous vehicle containing glucose and/or other auxiliaries. Tablets, capsuls, etc. can also be prepared by the established pharmaceutical procedures. These preparations may take unit dosage forms for application by the routes of administration suited for the purposes e.g. intravenous or subcutaneous preparations or preparations for direct injection at an effected area in the case of injectable solutions. The dosage for tumor-bearing warm-blooded animals is selected according to the clinical condition, route of administration, etc. and may generally range from about 0.1 to 100 mg/kg body weight or preferably from about 0.5 to 30 mg/kg body weight. The frequency of administration may be daily or at intervals of 2 to 7 days. For a sustained effective tissue concentration, the regimen of 1 to 3 divided doses daily or a drip infusion over a protracted time may also be feasible.

The compound (I) according to this invention has antifungal or antimycotic activity. Its antimycotic spectrum covers Trichopyton, *Crytococcus neoformans* and yeasts and, therefore, the compound is of value in the treatment and prevention of diseases (e.g. trichophytia) of which these organisms are causative agents.

Such an antimycotic preparation can be produced by the established pharmaceutical procedure and while the relative amount of the active compound in the preparation is not particularly critical, it may range from about 0.01 to 70 weight % or preferably about 0.1 to 5 weight % of the total composition when the preparation is intended for the treatment of trichophytia for instance. Such an antimycotic preparation can be conveniently applied in the conventional manner, e.g. by direct coating or spraying to the affected site once to several times daily.

The compound (I) is also active against phytopathogenic pests, especially fungi and, therefore, is useful as an agricultural fungicide for combating such plant diseases as rice blast, rice Helminthosporium leaf spot, rice stem rot, gray mold and cucumber anthracnose. Agricultural fungicides containing the compound (I) can be prepared in the conventional manner. The proper content of the active compound (I) is generally about 1–90% for emulsifiable concentrates, wettable powders and the like, and about 0.1–10% for oil solutions, dusts and the like, and about 5–50% for granular preparations. Emulsifiable concentrates, wettable powders and the like are preferably sprayed after adequate dilution with water or the like (e.g. 50–5,000-fold dilution). These agricultural fungicides can be applied in the conventional manner and generally in a proportion of about 10 to 300 g as the active compound to each 10 ares of land. The concentration of the active component in such fungicidal preparations is about 10 to 1000 ppm.

The compound (I) of this invention is only sparingly active against bacteria in general and yet is active against protozoa (e.g. Tetrahymena pyri. W.), which activity in association with the aforesaid antimycotic activity thereof makes the compound (I) of value as an antimycotic/antiprotozoal agent for the assay of bacterial ecologies in the soil, activated sludge, body fluids, etc. Thus, for example, in isolating useful bacteria from the soil, or in detecting the activity of bacteria alone to the exclusion of protozoa and fungi for operation or analysis of the activated sludge process in waste water treatment, selective growth of bacteria is possible without allowing fungi and protozoa present in the sample to grow. Specifically, the test sample is added to a liquid or solid culture medium, then 0.1 ml of an aqueous solution of the compound (I) having a concentration of about 10 μg/ml to 100 mg/ml is added, and incubation is performed.

The following production, test, working and dosage form examples are further illustrative but by no means limitative of this invention.

PRODUCTION EXAMPLE 1

2-Tetradecyloxyethyl 2-trimethylammonioethyl phosphate

In benzene were dissolved 12 g of 2-tetradecyloxyethyanol and 18 g of 2-bromoethyl phosphorodichloridate, and following dropwise addition of 5.9 g of pyridine under ice-cooling, the mixture was stirred at room temperature for 3 hours. The benzene was distilled off, water was added and the solution refluxed for 1 hour and 30 minutes. After cooling, the reaction mixture was extracted with ether and the extract was concentrated to dryness. The residue was dissolved in 20% trimethylamine-toluene and heated in a sealed tube at 60° C. for 2 days. After completion of the reaction, the solvent was replaced with methanol, 16.6 g of silver carbonate was added thereto, and the mixture was refluxed. The hot mixture was filtered and the filtrate was concentrated to dryness to give a crude product, which was purified by column chromatography using silica gel (developing solvent: first MeOH; second, $CHCl_3$—MeOH—$H_2O$) and recrystallized from chloroform-acetone to give 9.4 g (48%) of the desired product as a white powder.

Infrared absorption spectrum (KBr) $cm^{-1}$: 3400, 2920, 2850, 1630, 1460, 1220, 1130, 1090, 1060.

Elemental Analysis: Calcd. for $C_{21}H_{46}NO_5P.1.5H_2O$: C, 55.98; H, 10.96; N, 3.11; P, 6.88. Found: C, 56.28; H, 11.52; N, 3.46; P, 7.02.

PRODUCTION EXAMPLE 2

2-Tridecyloxyethyl 2-trimethylammonioethyl phosphate

In benzene were dissolved 3.8 g of 2-n-tridecyloxyethanol and 5.7 g of 2-bromoethyl phosphorodichloridate, and following dropwise addition of 1.85 g of pyridine under ice-cooling, the mixture was stirred at room temperature. The reaction mixture was treated by the procedure of Production Example 1 including hydrolysis, quaternization, dehalogenation, purification by silica gel column chromatography and recrystallization from chloroform-acetone to give 2.2 g (34%) of the desired product. It was hygroscopic.

Elemental Analysis: Calcd. for $C_{20}H_{44}NO_5P.0.5H_2O$: C, 57.39; H, 10.83; N, 3.35; P, 7.40. Found: C, 57.61; H, 11.17; N, 3.68; P, 7.25.

PRODUCTION EXAMPLE 3

2-Oleyloxyethyl 2-trimethylammonioethyl phosphate

In benzene were dissolved 4.0 g of 2-[(Z)-9-octadecen-1-yl)oxyethanol and 4.6 g of 2-bromoethyl phosphorodichloridate, and following dropwise addition of 1.5 g of pyridine under ice-cooling, the mixture was stirred at room temperature. The reaction mixture was treated by the procedure of Production Example 1 including hydrolysis, quaternization, purification by silica gel column chromatography and recrystallization from chloroform-acetone to give 0.52 g (9%) of the desired product.

Elemental Analysis: Calcd. for $C_{25}H_{52}NO_5P.H_2O$: C, 60.58; H, 10.98; N, 2.83; P, 6.25. Found: C, 60.59; H, 11.28; N, 3.07; P, 6.31.

PRODUCTION EXAMPLE 4

2-Dodecyloxyethyl 2-trimethylammonioethyl phosphate

In 31 ml of benzene was dissolved 4.2 g (18.23 mmol) of 2-dodecyloxyethanol, and following addition of 6.62 g of 2-bromoethyl pohsphorodichloridate and 2.1 g of pyridine, the mixture was stirred at room temperature. The reaction mixture was concentrated to dryness under reduced pressure, water was added to the residue, and the mixture was refluxed. After cooling, 5 ml of conc. hydrochloric acid was added, extraction was carried out with ether, and the ether layer was concentrated to dryness. The residue was dissolved in 20% $NMe_3$-toluene (w/w) and stirred at room temperature. The reaction mixture was concentrated to dryness under reduced pressure, the residue was dissolved in methanol, and 4.2 g of $Ag_2CO_3$ was added thereto. The mixture was stirred vigorously, the insoluble matter was filtered off, and the mother liquor was concentrated to dryness under reduced pressure. The residue was purified by silica gel column chromatography [eluent: MeOH and CHCl₃—MeOH—H₂O (65:25:2)] to give the desired product as colorless crystals.

TLC [silica gel, CHCl₃—MeOH—H₂O (65:25:4)]: Single spot, Rf=0.13.

Infrared absorption spectrum (film) cm$^{-1}$: 3390, 2930, 2850, 1650, 1480, 1240, 1080, 1060, 960, 920, 785(sh), 755.

Elemental Analysis: Calcd. for $C_{19}H_{40}NO_5P \cdot \frac{1}{2}H_2O$: C, 56.69; H, 10.27; N, 3.48; P, 7.70. Found: C, 56.61; H, 10.57; N, 3.55; P, 7.63.

PRODUCTION EXAMPLE 5

2-Tetradecyloxyethyl 2-aminoethyl phosphate

In benzene was dissolved 1.6 g of 2-tetradecyloxyethanol, and following addition of 2.48 g of 2-phthalimidoethyl phosphorodichloridate and 0.636 g of pyridine, the mixture was stirred at room temperature. The reaction mixture was concentrated to dryness under reduced pressure, the resulting residue was dissolved in 70% pyridine and the solution was heated at 70° C. for 30 minutes. The pyridine was distilled off under reduced pressure, followed by addition of water, conc. hydrochloric acid and ether to the residue. The mixture was stirred vigorously, and the ether layer was taken and concentrated to dryness under reduced pressure. The residue was dissolved in methanol, 1.5 g of hydrazine hydrate was added and the mixture was refluxed. The insoluble matter was filtered off and the filtrate was concentrated to dryness under reduced pressure. The residue was purified by silica gel column chromatography and recrystallized from methanol to give a colorless crystalline powder (1.7 g).

TLC [silica gel, CHCl₃—MeO—H₂O (65:25:4)] Single spot, Rf=0.12.

Infrared absorption spectrum (KBr) cm$^{-1}$: 3450, 2930, 2860, 1650, 1560, 1470, 1255, 1230, 1140, 1095, 1080, 1020, 1005, 920, 840, 760.

Elemental Aanalysis: Calcd. for $C_{18}H_{40}NO_5P$: C, 56.67; H, 10.57; N, 3.67; P, 8.12. Found: C, 56.67; H, 10.30; N, 3.82; P, 8.19.

PRODUCTION EXAMPLE 6

2-Octadecyloxyethyl 2-aminoethyl phosphate

In benzene was dissolved 1.8 g of octadecyloxyethanol and 2.24 g of 2-phthalimidoethyl phosphorodichloridate, and following addition of 0.88 g of pyridine, the mixture was stirred at room temperature for 2 hours. This reaction mixture was treated by the procedure of Production Example 5 to give a colorless powder (1.7 g).

TLC [silica gel, CHCl₃—MeOH—H₂O (65:25:4)] Single spot, Rf =0.12.

Infrared absorption spectrum (KBr) cm$^{-1}$: 3400, 2900, 2850, 1630, 1550, 1460, 1250, 1220, 1150, 1075, 1010, 910, 830, 750.

Elemental Analysis: Calcd. for $C_{22}H_{48}NO_5P \cdot 0.3H_2O$: C, 59.64; H, 11.06; N, 3.16; P, 6.99. Found: C, 59.66; H, 10.97; N, 3.36; P, 7.19.

PRODUCTION EXAMPLE 7

2-Pentadecyloxyethyl 2-trimethylammonioethyl phosphate

In benzene were dissolved 5.0 g of 2-pentadecyloxyethanol and 7.1 g of 2-bromoethyl pohsphorodichloridate, and following dropwise addition of 2.3 g of pyridine under ice-cooling, the mixture was stirred at room temperature. The benzene was distilled off and water was added. The mixture was refluxed, cooled, extracted with ether, and concentrated to dryness. The residue was dissolved in 20% trimethylamine-toluene and heated in a sealed tube at 60° C. After completion of the reaction, the solvent was replaced with methanol, 6.6 g of silver carbonate was added, and the mixture was refluxed for 1.5 hours. The hot mixture was filtered and the filtrate was concentrated to dryness to give a crude product. It was purified by silica gel column chromatography and recrystallized from chloroform-acetone to give 2.37 g (30%) of the desired product.

Elemental Analysis: Calcd. for $C_{22}H_{48}NO_5P \cdot 0.5H_2O$: C, 59.17; H, 11.06; N, 3.14. Found: C, 59.27; H, 12.37; N, 3.22.

PRODUCTION EXAMPLE 8

2-Pentadecyloxyethyl 2-pyridinioethyl phosphate

In benzene were dissolved 4.4 g of 2-pentadecyloxyethanol and 5.7 g of 2-bromoethyl phosphorodichloridate, and following dropwise addition of 1.86 g of pyridine under ice-cooling, the mixture was stirred at room temperature. The benzene was distilled off and water was added. The mixture was refluxed, cooled, extracted with ether, and concentrated to dryness. The residue was dissolved in pyridine, refluxed, stirred, and then concentrated to dryness. Methanol and then 5.3 g of silver carbonate were added to the residue and the mixture was refluxed. The hot mixture was filtered and the filtrate was concentrated to dryness to give a crude product. It was purified by silica gel column chromatography and recrystallized from chloroform-acetone to give 3.41 g (57%) of the desired product.

Elemental Analysis: Calcd. for $C_{24}H_{46}NO_5P \cdot 0.25H_2O$: C, 62.11; H, 10.10; N, 3.02. Found: C, 62.03; H, 10.06; N, 3.13.

PRODUCTION EXAMPLE 9

2-Tetradecyloxyethyl 2-pyridinioethyl phosphate

In benzene were dissolved 5.1 g of 2-tetradecyloxyethanol and 7.6 g of 2-bromoethyl phosphorodichloridate, and following dropwise addition of 2.5 g of pyridine, the mixture was stirred at room temperature for 3 hours. The solvent was then distilled off and water was added. The mixture was refluxed, cooled, extracted with ether and concentrated to dryness. To the residue was added pyridine, and the solution was refluxed, stirred at room temperature and concentrated to dryness. Methanol and then 7.06 g of silver carbonate were added to the residue and the mixture was refluxed. The hot mixture was filtered and the filtrate was concentrated to dryness to give a crude product. It was purified by silica gel column chromatography and recrystallized from chloroform-acetone to give 4.3 g (49%) of the desired product.

NMR(CDCl₃)δ: 0.87(3H), 1.23(24H), 3.26–4.56(8H), 4.91–5.17 (2H), 8.10–8.63(3H), 9.56(2H,J=6.0 Hz).

Elemental Analysis: Calcd. for $C_{23}H_{42}NO_5P \cdot 0.5H_2O$: C, 61.04; H, 9.58; N, 3.10; P, 6.84. Found: C, 60.92; H, 9.85; N, 3.11; P, 6.63.

PRODUCTION EXAMPLE 10

2-Octadecyloxyethyl 2-pyridinioethyl phosphate 2.73 g of 2-octadecyloxyethanol and 3.16 g of 2-bromoethylphosphorodichloridate were reacted and purified by the procedure of Production Example 5 to give 840 mg (19.3%) of colorless powder.

Elemental Analysis: Calcd. for $C_{27}H_{50}NO_5P$: C, 64.90; H, 10.09; N, 2.80; P, 6.20. Found: C, 65.03; H, 10.19; N, 3.07; P, 5.74.

Infrared absorptoin spectrum (KBr) $cm^{-1}$: 2910, 2850, 1220, 1090.

NMR(CDCl$_3$) δ: 0.88(3H), 1.27(32H), 3.27–4.07(6H), 4.33(2H), 4.97(2H), 8.03(2H), 8.43(1H), 9.28(2H).

PRODUCTION EXAMPLE 11

2-Tetradecyloxyethyl 2-[N,N-dimethyl-N-(3-methoxycarbonylpropyl)]ammonioethyl phosphate 6.23 g of 2-tetradecyloxyethyl 2-bromoethylphosphate was dissolved in 10.09 g of methyl γ-dimethylamino-n-butylate and reacted for 17 hours at 70° C. while stirring. After cooling, the solution was diluted with methanol, added 3,85 g of silver carbonate and stirred vigorously for 1 hour at room temperature. Insolubles were filtered off and the filtrate was concentrated to dryness under reduced pressure. The resulting residue was purified by silica gel column chromatography to give 4.49 g (63.3%) of desired product.

Elemental Analysis: Calcd. for $C_{25}H_{52}NO_7P \cdot 1.6H_2O$: C, 55.76; H, 10.33; N, 2.60. Found: C, 55.75; H, 10.11; N, 2.85.

Infrared absorption spectrum (film) $cm^{-1}$: 3380, 2920, 2850, 1735, 1640, 1460, 1220, 1075, 950.

NMR(CDCl$_3$) δ: 0.93(3H), 1.25(24H), 2.00–2.33(2H), 3.30(3H), 3.43(3H), 3.67(3H), 3.16–3.93(8H), 4.10–4.50(4H).

PRODUCTION EXAMPLE 12

2-Tetradecyloxyethyl 2-[N-(3-carboxypropyl)-N,N-dimethyl]ammonioethyl phosphate 2.85 g of the ester compound obtained by Production Example 11 was dissolved in 57 ml of ethanol and treated with 2.16 g of 28% sodium methylate-methanol solution for 18 hours at room temperature while stirring. The solution was neutralized with 0.4 N hydrogen chloride-methanol solution, diluted with the same volume of methylenechloride and then the insolubles were filtered off. The filtrate was concentrated to dryness under reduced pressure and the resulting residue was purified by silica gel column chromatography to give 2.0 g (72%) of desired products.

Elemental Analysis: Calcd. for $C_{24}H_{50}NO_7P$: C, 58.16; H, 10.17; N, 2.83. Found: C, 58.01; H, 10.11; N, 2.89.

Infrared absorption spectrum (KBr) $cm^{-1}$: 3430, 2960, 2930, 2850, 1705, 1502, 1475, 1265, 1230, 1215, 1100, 1080, 1055, 958, 870, 830, 780.

NMR (CD$_3$OD/CDCl$_3$) δ: 0.93(3H), 1.29(24H), 1.86–2.22(2H), 2.26–2.70(2H), 3.20(6H), 3.43–3.80(6H), 3.83–4.20(4H), 4.20–4.53(2H).

PRODUCTION EXAMPLE 13

2-Octadecyloxyethyl 2-trimethylammonioethyl phosphate

The desired product was obtained by the same manner as Production Example 3 as colorless needles.

Infrared absorption spectrum (KBr) $cm^{-1}$: 2920, 2850, 1460, 1220, 1080.

Elemental Analysis: Calcd. for $C_{25}H_{54}NO_5P \cdot 1.5 H_2O$ C, 59.26; H, 11.34; N, 2.76; P, 6.11. Found: C, 59.11; H, 11.52; N, 2.89; P, 6.25.

TEST EXAMPLE 1

The cell proliferation inhibitory activity (GD$_{50}$) and differentiation inducing activity of the compound of this invention against human promyelocytic leukemia cell HL-60 are shown in Table 1. The assays were performed by the method described for example in R. Gallo et al, Blood. vol. 54, No. 3, 713 (1979).

TABLE 1

Effect on human promyelocytic leukemia cells HL-60

| Test compound (Production example No.) | Cell proliferation inhibitory activity GD$_{50}$ (μg/ml)*[1] | Differentiation (Morphology)*[2] |
|---|---|---|
| 1 | 3.8 | +++ |
| 6 | 3.0 | ++ |
| 7 | 1.2 | ++ |
| 8 | 3.4 | +++ |
| 9 | 4.1 | +++ |
| 10 | 1.5 | + |
| 11 | 2.5 | + |
| 12 | 1.5 | + |

*[1] 5 days' culture
*[2] Activity at the compound concentration of 6 μg/ml

TEST EXAMPLE 2

The antiprotozoal and antimycotic activities of the compound of this invention are given in Tables 2 and 3, respectively.

The antiprotozoal activity values given in Table 2 were assayed using *Tetrahymena pyriformis* W as the test organism and an assay medium composed of 20 g tryptose peptone (Difco), 1 g yeast extract, 2 g glucose, 1000 ml distilled water and 10 ml 1 M phosphate buffer, pH 7.0. Thus, the strain was incubated at 28° C. for 44 to 48 hours and the minimal inhibitory concentration (MIC) of the compound (I) was determined by the broth dilution method.

The antimycotic activity values presented in Table 2 were assayed using *Cryptococcus neoformans* as the test organism. Thus, a paper disk (8 mm dia.) was dipped into an aqueous solution of the test compound (3 mg/ml), dried in the air and set in position on an agar medium. The medium was incubated at 37° C. for 2 days, at the end of which time the diameter of the zone of inhibition was measured. When the diameter of the zone was not larger than 8 mm, 8–10 mm, 10–20 mm and larger than 20 mm, the activity was judged as −, ±, + and ++, respectively.

Referring to the antifungal activity values given in Table 3, a variety of typical phytopathogenic fungi were used as test organisms, and the minimal inhibitory concentration (MIC) values were determined by the serial dilution method using 1% glucose-bouillon agar medium.

TABLE 2

Antiprotozoal and antimycotic activities

| Test compounds (Example No.) | Tetrahymena pyriformis W MIC (μg/ml) | Cryptococcus Diameter of inhibition zone (mm)* |
|---|---|---|
| 1 | 0.4 | ++ |
| 2 | 0.4 | ++ |
| 3 | 0.4 | ++ |
| 4 | 0.4 | + |
| 5 | 4 | ± |
| 6 | >4 | ± |
| 7 | ≦1 | + |
| 8 | 4 | + |
| 9 | 4 | ++ |
| 10 | 4 | ... |
| 11 | 4 | ... |
| 12 | 0.4 | ... |

*value at the concentration of 3 mg/ml

TABLE 3

Antifungal activity of the compound of this invention

| | MIC (μg/ml) Test compound (Example No.) | | | | |
|---|---|---|---|---|---|
| Test phytopathogenic fungus | 1 | 2 | 3 | 4 | 5 |
| (1) *Pyricularia oryzae* (rice blast) | 3.12 | 6.25 | 1.56 | 12.5 | 25 |
| (2) *Helminthosporium oryzae* (rice Helminthosporium leaf spot) | 12.5 | 6.25 | 6.25 | 12.5 | >100 |
| (3) *Botrytis cinerea* (gray mold) | 12.5 | 12.5 | 3.12 | 25 | 50 |
| (4) *Helminthosporium sigmordeum* (rice stem rot) | 3.12 | 6.25 | 6.25 | 25 | >100 |
| (5) *Sclerotinia sclerotiorum* (kidney bean stem rot) | 50 | 12.5 | 100 | 100 | 100 |
| (6) *Colletotrichum lagenarium* (cucumber anthracnose) | 3.12 | 3.12 | 6.25 | 6.25 | 25 |
| (7) *Aspergillus niger* (black mold) | 12.5 | 12.5 | 25 | 25 | 25 |
| (8) *Penicillium niger* (blue mold) | 12.5 | 25 | 50 | 25 | 50 |
| (9) *Saccharomyces cerevisiae* (brewer's yeast) | <3.12 | 6.25 | 12.5 | 25 | 25 |

TEST EXAMPLE 3

Test for antitumor activity of 2-octadecyloxy 2-pyridinioethyl phosphate (Production Example 10)

1. Antitumor activity against sarcoma 180

A group of five ICR mice was administered with 500 μg/mouse of the test compound dissolved in physiological saline. On the fourth day from the administration, $1 \times 10^5$ cells of sarcoma 180 per mouse were transplanted introperitonally. Average survival period of the test group was 29.8 days, while that of the control group (five mice) was 9.6 days. The survival rates of the test group against the control group T/C reached 310%.

2. Antitumor activity against MM46 mammarian carcinoma

MM46 mammarian carcinoma cells ($1 \times 10^5$) was transplanted intraperitoneally to each of five C3H/He mice group. From five days to two days before the transplantation and from two day to five days after the transplantation, eight days in total. 250 μg/mouse/day of the test compound was administered to the test group, once daily. Survival period of three of the test group was not less than 60 days, and that of the remaining two was 23 days in average. On the other hand, the average survival period of mice of the control group was 14.2 days.

3. Activation of macrophage

300 μg/mouse of the test compound was administered to a group of the test animals (five ICR mice) intraperitoneally. Four days later, the peritoneal cells were collected, and the numbers of the total cells and adsorbed cells were measured. Both the numbers were observed about five times as much as those of the control group.

Macrophage of a determined number of cells was collected, which was suspended in Hanks' solution. Activated oxygen generated by PMA-stimulation was determined to reveal that the amount of activated oxygen from the test group was about three times as much as that from the control group. This means that the test compound serves to increase and activate macrophage in living body.

DOSAGE FORM EXAMPLE 1

Injectable preparation: 2-tetradecyloxyethyl 2-trimethylammonioethyl phosphate (80 g) is dissolved in 1 liter of distilled water, the solution is passed through a sterilization filter, poured into 1,000 vials (1 ml per vial) and lyophilized, and the vials are tightly stoppered.

Separately, a solution containing xylitol or mannitol (100 g in 2 liters) in distilled water for injection is poured into 1,000 ampules for injectable solution (2 ml per ampule) in an aseptic manner, and the ampules are sealed by fusing.

For administration, the powder in one vial is dissolved in the above-mentioned xylitol (or mannitol) solution in one ampule.

DOSAGE FORM EXAMPLE 2

Tablets, each weighing 370 mg and having a diameter tablets of 9.5 mm, are prepared in a conventional manner by mixing the ingredients:

| | |
|---|---|
| (1) Octadecyloxyethyl 2-aminoethyl phosphate | 100 mg per tablet |
| (2) Lactose | 200 mg per tablet |
| (3) Corn starch | 51 mg per tablet |
| (4) Hydroxypropylcellulose | 9 mg per tablet | followed by granulation, addition of corn starch (8 mg per tablet) and magnesium stearate (2 mg per tablet) and tableting.

DOSAGE FORM EXAMPLE 3

Tablets containing 2-tetradecyloxyethyl 2-pyridinioethyl phosphate are prepared in the same manner as in Dosage Form Example 2, and coated with a solution of hydropropylmethylcellulose phthalate (14 mg per tablet) and castor oil (1 mg per tablet) in an acetone-ethanol (4:6) mixture, the concentration of the solutes being 7%. Thus are obtained enteric coated tablets.

What is claimed is:

1. A compound, inclusive of salts thereof, of the formula:

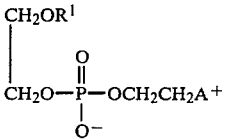

wherein
R$^1$ is C$_{8-26}$ aliphatic hydrocarbon residue, and
A$^+$ is cyclic ammonio.

2. The compound according to claim 1, wherein the aliphatic hydrocarbon residue is C$_{10-20}$ alkyl, C$_{10-20}$ alkenyl or C$_{14-24}$ aralkyl.

3. The compound according to claim 1, wherein A$^+$ is pyridinio, oxazolio, thiazolio, pyridazinio, quinolinio or isoquinolinio.

4. The compound according to claim 1, which is 2-octadecyloxyethyl 2-pyridinioethyl phosphate.

5. A compound of claim 1 wherein A$^+$ is pyridinio, thiazolo or oxazolo.

6. A compound of claim 1 wherein A$^+$ is quinolino or isoquinolino.

* * * * *